US011925749B2

(12) United States Patent
Anderson, Jr. et al.

(10) Patent No.: US 11,925,749 B2
(45) Date of Patent: Mar. 12, 2024

(54) VENTING OF PHARMACEUTICAL DRUG DELIVERY DEVICE FOR AIR FLOW AND HUMIDITY CONTROL

(71) Applicant: Funai Electric Co., Ltd., Osaka (JP)

(72) Inventors: James D. Anderson, Jr., Lexington, KY (US); Michael A. Marra, III, Lexington, KY (US)

(73) Assignee: Funai Electric Co., Ltd. (JP)

( * ) Notice: Subject to any disclaimer, the term of this patent is extended or adjusted under 35 U.S.C. 154(b) by 546 days.

(21) Appl. No.: 17/205,280

(22) Filed: Mar. 18, 2021

(65) Prior Publication Data

US 2022/0296828 A1 Sep. 22, 2022

(51) Int. Cl.
*A61M 15/02* (2006.01)
*A61M 15/00* (2006.01)
*A61M 15/08* (2006.01)

(52) U.S. Cl.
CPC ...... *A61M 15/025* (2014.02); *A61M 15/0025* (2014.02); *A61M 15/0086* (2013.01); *A61M 15/08* (2013.01); *A61M 2206/10* (2013.01)

(58) Field of Classification Search
CPC ....... A61M 15/02–025; A61M 15/0025–0026; A61M 15/0086–0088; A61M 15/08; A61M 2206/10; A61M 2206/12; A61M 2206/16–18; A61M 11/041; A61M 15/0028–0061; A61M 15/0085; A61M 11/005; A61M 11/02; A61M 2210/0618
USPC .................................................... 128/200.14
See application file for complete search history.

(56) References Cited

U.S. PATENT DOCUMENTS

| 6,257,232 | B1 * | 7/2001 | Andersson ........ A61M 15/0068 |
| | | | 128/203.15 |
| 6,810,875 | B2 * | 11/2004 | Staniforth ............ A61M 11/002 |
| | | | 128/200.14 |
| 8,377,009 | B2 | 2/2013 | Sullivan et al. |
| 8,656,909 | B2 | 2/2014 | Godfrey et al. |
| 9,492,625 | B2 * | 11/2016 | Smyth ............... A61M 15/0028 |
| 9,636,430 | B2 | 5/2017 | Gruenbacher et al. |
| 10,668,230 | B2 | 6/2020 | Giroux |
| 2010/0083963 | A1 | 4/2010 | Wharton et al. |
| 2010/0276457 | A1 | 11/2010 | Petit et al. |

(Continued)

FOREIGN PATENT DOCUMENTS

CN 212491195 U 2/2021

*Primary Examiner* — Elliot S Ruddie
(74) *Attorney, Agent, or Firm* — Luedeka Neely, P.C.

(57) ABSTRACT

A pharmaceutical drug delivery device and method of preventing drying out and drooling of an ejection head for the drug delivery device. The device includes a drug delivery device body; a fluid outlet nozzle attached to the drug delivery device body; and a fluid jet ejection cartridge containing a liquid pharmaceutical drug disposed in the drug delivery device body. A fluid ejection head is attached to the fluid jet ejection cartridge and the fluid ejection head is in fluid flow communication with the fluid outlet nozzle. An elongate, serpentine air flow path is provided between and outer surface of the fluid jet ejection cartridge and an inner surface of the fluid outlet nozzle. The elongate, serpentine air flow path provides a reduced pressure differential adjacent to a surface of the fluid ejection head upon use of the drug delivery device and provides a humidification zone.

16 Claims, 7 Drawing Sheets

(56) References Cited

U.S. PATENT DOCUMENTS

2011/0253752 A1* 10/2011 Godfrey ................ A61M 11/08
　　　　　　　　　　　　　　　　　　　　　　222/566
2018/0369508 A1　12/2018 Voon Hollen et al.
2019/0015855 A1　 1/2019 Hoxie et al.

* cited by examiner

VENTING OF PHARMACEUTICAL DRUG DELIVERY DEVICE FOR AIR FLOW AND HUMIDITY CONTROL

TECHNICAL FIELD

The disclosure is directed to inhalation drug delivery systems and in particular to inhalation devices that have improved air flow and humidity control.

BACKGROUND AND SUMMARY

Nasal spray devices have become important methods for delivering drugs to patients. Such nasal spray devices are more convenient to use than the administration of drugs through IV or injection. Nasal spray devices also provide higher bioavailability of drugs compared to oral administration of drugs. The absorption of drugs through nasal spray devices is more rapid compared to the absorption of drugs administered orally since drugs delivered by nasal spray devices directly enter the blood stream making their effect more immediate.

FIG. 1 is a cross sectional view, not to scale, of anatomy of a nasal cavity 10 of a person. A portion of the brain 14 is shown above the nasal cavity 10. An olfactory bulb 14 is disposed between the brain 12 and a cribriform plate 16. An olfactory mucosa is below the cribriform plate 16. The nasal cavity also includes a superior turbinate 20, a middle turbinate 22, respiratory mucosa 24 and an inferior turbinate 26. Item 28 represents the palate. Injection of a pharmaceutical drug mist enters the nasal cavity 10 through the nostrils 30 and squamous mucosa 32. In order to achieve proper delivery of drugs to the blood stream using a nasal spray device, the drugs must be delivered to the respiratory mucosa which is highly vascularized. Two areas that are highly vascularized are the olfactory region and the respiratory region. The respiratory region contains turbinates which increase the surface area available for drug absorption.

Conventional methods for delivering drugs via the nasal cavity include medicine droppers, multi-spray bottles with spray tips, single-dose syringes with spray tips, and dry powder systems. Accordingly, conventional drug delivery devices are typically designed to deliver a specific drug to a nasal cavity and each device cannot be adapted for delivering a wide range of drugs via a nasal cavity route. Many of the conventional methods for nasal drug delivery rely on pressurized containers to inject a mist of fluid into the nasal cavity. Accordingly, the drug delivery devices are typically designed for a specific drug and cannot be adapted to administer a different drug.

Despite the availability of a variety of devices for delivering drugs via a nasal cavity route, there remains a need for a nasal drug delivery device that can be adapted to deliver a variety of drugs. One such device is an on-demand fluid jet delivery device. Conventional fluid jet delivery devices operate to eject fluid to a substrate under ambient atmospheric pressure. However, when a nozzle of a nasal applicator is used, the nozzle is inserted into one nostril of a user which closes off the nostril to the ambient atmosphere. When the user breathes in, a low pressure area is generated in the nozzle of the device. If the nasal applicator uses a fluid jet delivery ejection head attached to a fluid cartridge, the low pressure will provide a pressure differential that will cause fluid inside of fluid cartridge to drool out of the ejection head and puddle on the surface thereof. Such fluid puddling interferes with fluid jetting from the ejection head and delivery of a precise amount of pharmaceutical drug to the user.

Another problem associated with using a fluid jet ejector device to administer drugs to a user's nasal cavity is that fluid may dry out on the ejection head between uses and interfere with fluid ejected through fluid nozzles on the ejection head causing misdirection of fluid and mis-firing of fluid ejectors. Accordingly, what is needed is an improved nasal applicator that is designed to prevent drooling of fluid from a fluid cartridge having a fluid jet delivery device to eject fluid into a nasal cavity of a user. The device must also prevent fluid from drying out on the ejection head between uses of the device.

In view of the foregoing an embodiments of the disclosure provide a pharmaceutical drug delivery device and method of preventing drying out and drooling of an ejection head for the drug delivery device. The device includes a drug delivery device body; a fluid outlet nozzle attached to the drug delivery device body; and a fluid jet ejection cartridge containing a liquid pharmaceutical drug disposed in the drug delivery device body. A fluid ejection head is attached to the fluid jet ejection cartridge and the fluid ejection head is in fluid flow communication with the fluid outlet nozzle. An elongate, serpentine air flow path is provided between and outer surface of the fluid jet ejection cartridge and an inner surface of the fluid outlet nozzle. The elongate, serpentine air flow path provides a reduced pressure differential adjacent to a surface of the fluid ejection head upon use of the drug delivery device and provides a humidification zone.

In one embodiment, there is provided a method for reducing a pressure differential on a fluid jet ejection head for a nasal spray device. The method includes providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge. A sealing material is inserted between an outer surface of the fluid jet ejection cartridge and an inner surface of the fluid outlet nozzle. The sealing material contains an elongate, serpentine air flow path therein to provide a reduced pressure differential adjacent to a surface of the fluid ejection head upon use of the drug delivery device. The nasal spray device is activated while flowing air through the drug delivery device body and elongate, serpentine air flow path when the fluid outlet nozzle is inserted into the nasal passage of a user thereby preventing fluid from drooling from the fluid ejection head.

In another embodiment, there is provided a method for preventing a surface of a fluid jet ejection head for a nasal spray device from drying out between uses. The method includes providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge. A sealing material is inserted between an outer surface of the fluid jet ejection cartridge and an inner surface of the fluid outlet nozzle. The sealing material contains an elongate, serpentine air flow path therein to provide a humidification zone in the drug delivery device adjacent to a surface of the fluid ejection head between uses of the drug delivery device. The fluid outlet nozzle is plugged with a cap to prevent drying out of the surface of the fluid jet ejection head.

In another embodiment, the elongate, serpentine air flow path has a length to cross-sectional area ratio of about 30:1 to about 100:1.

In another embodiment, the elongate, serpentine air flow path is provided by a multi-chamber sealing material disposed in the fluid outlet nozzle between an interior surface of the fluid outlet nozzle and an exterior surface of the fluid jet ejection cartridge, wherein the multi-chamber sealing material includes air chambers and notches for air flow between adjacent air chambers.

In some embodiments, the elongate, serpentine air flow path is provided between an exterior surface of the fluid jet ejection cartridge and the air chambers of the multi-chamber sealing material.

In other embodiments, the elongate, serpentine air flow path is provided between the interior surface of the fluid outlet nozzle and an exterior surface of a sealing material disposed in the fluid outlet nozzle adjacent to the fluid jet ejection cartridge.

In some embodiments, a plug is provided to cap off the fluid outlet nozzle and create the humidification zone in the drug delivery device between uses.

An advantage of disclosed embodiments is that a single sealing material can be used to provide both reduced pressure differential on a jet ejection head during use of the pharmaceutical device and can provide a humidification zone in the device when capped to prevent the ejection head from drying out.

DETAILED DESCRIPTION

Figure 1:
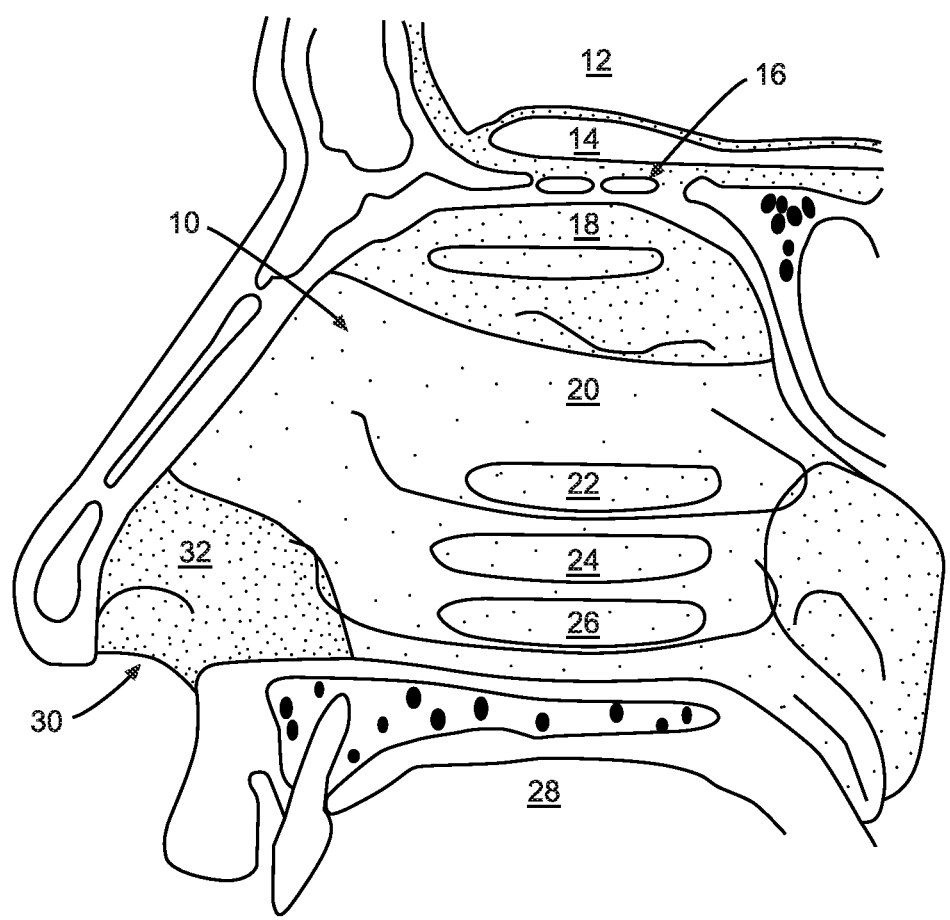
FIG. 1 is a cross-sectional representation, not to scale, of a portion of a nasal cavity and scull of a person.
Figure 2:
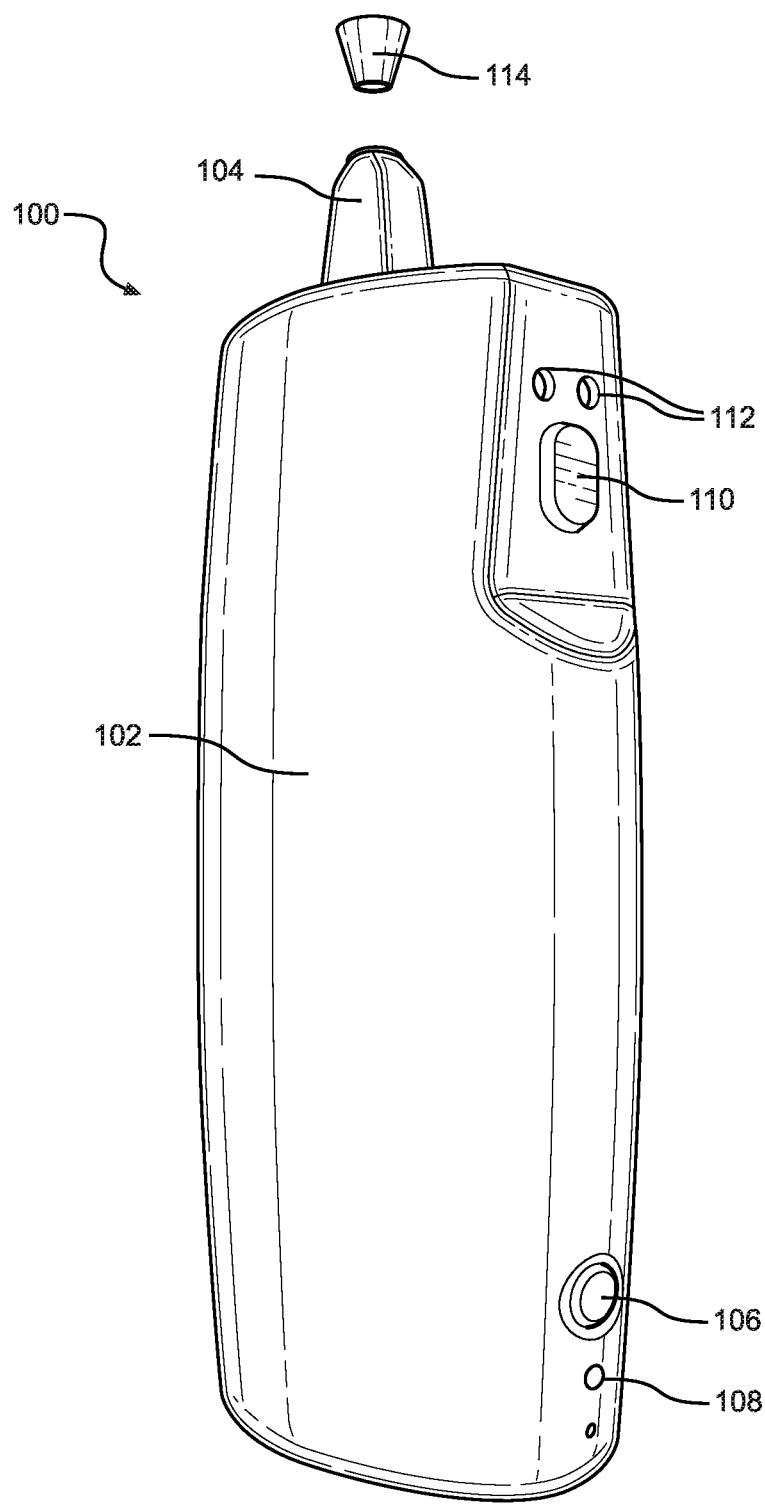
FIG. 2 is a perspective view, not to scale of a pharmaceutical drug delivery device according to an embodiment of the disclosure.

An illustration of a pharmaceutical drug delivery device 100 is illustrated in FIG. 2. The device includes a drug delivery device body 102, having a fluid outlet nozzle 104 attached to the drug delivery device body 102. A power button 106 is provided to activate the drug delivery device as indicated by an LED 108. During use of the device 100, a dispense button 110 is pressed and fluid delivery is indicated by LED's 112. When not in use, a plug 114 may be inserted into the device 100 to prevent fluid from drying out on a fluid jet ejection head used to deliver the pharmaceutical drug to a user. The drug delivery device body 102 also contains a power source and a controller for controlling the ejection of fluid from the fluid jet ejection head.

Figure 3:
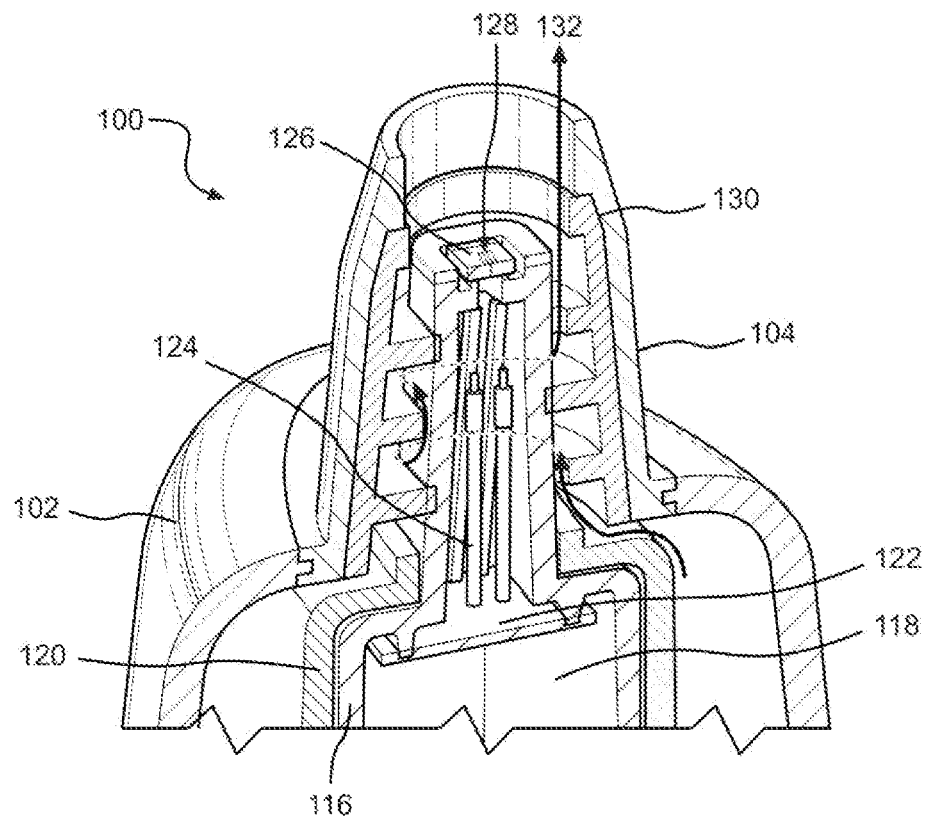
FIG. 3 is a partial perspective, cross-sectional view, not to scale, of the drug delivery device of FIG. 2 containing a sealing material according to a first embodiment of the disclosure.

With reference to FIG. 3, a cross-sectional, perspective view of a portion of the drug delivery device 100 is illustrated. The drug delivery device 100 includes the drug delivery device body 102 for holding a fluid jet ejection cartridge 116 containing a pharmaceutical fluid 118 in a cartridge holder 120. A fluid filter 122 is disposed in the cartridge 116 to filter the fluid flowing through filter tower structures 124 to a fluid jet eject ejection head 126. In some embodiments, the fluid cartridge 116 may also contain a backpressure control device such as a bladder or foam for inducing a backpressure on the fluid jet ejection head 126. The fluid jet ejection head 126 may be selected from any of the conventional types of fluid jet ejection heads, including but not limited to, thermal jet ejection heads, bubble jet ejection heads, piezoelectric jet ejection heads, and the like. Each of the foregoing ejection heads can produce a spray of fluid on demand.

As set forth above, when the fluid outlet nozzle 104 is inserted into the nostril 30 of a user, and the user inhales, a low pressure area is formed adjacent to an exposed surface 128 of the ejection head 126. This low pressure area creates a "pressure differential" between the surface 128 of the ejection head 126 and the fluid in the cartridge 116. The pressure differential can cause unwanted flow or drooling of fluid from the ejection head 126. Accordingly, in order to reduce the pressure differential adjacent to the surface 128 of the ejection head 126, a sealing material 130 containing a serpentine air flow path 132, is provided in the fluid outlet nozzle 104 surrounding the cartridge 116. In one embodiment, the sealing material 130 contains alternating notches 134 that are in fluid flow communication with adjacent air chambers 136 so that a serpentine path through the sealing material 130 is provided.

The sealing material for use with the device 100 may be selected from a wide variety of sulfur-free resilient materials such as natural or synthetic rubber, and thermoplastic or thermoset elastomers having a shore A durometer of less than about 60 that are compatible with the fluids being ejected from the ejection head 126. Examples of such materials include, but are not limited to natural rubber, EPDM rubber, and a dynamically vulcanized alloy consisting mostly of fully cured EPDM rubber particles encapsulated in a polypropylene (PP) matrix, available from ExxonMobil under the tradename SANTOPRENE. The sealing material 130 can be molded and shaped to provide the serpentine air flow path 132 therein and can provide a seal between the fluid jet ejection cartridge 116 and the fluid outlet nozzle 104. It will be appreciated that the drug delivery device body 102 of the device 100 is not air-tight and thus provides inlet air flows from a variety of locations such as from the buttons 106 and 110 and any opening provided for inserting the fluid jet ejection cartridge 116 into the drug delivery device body 102.

Figure 4:
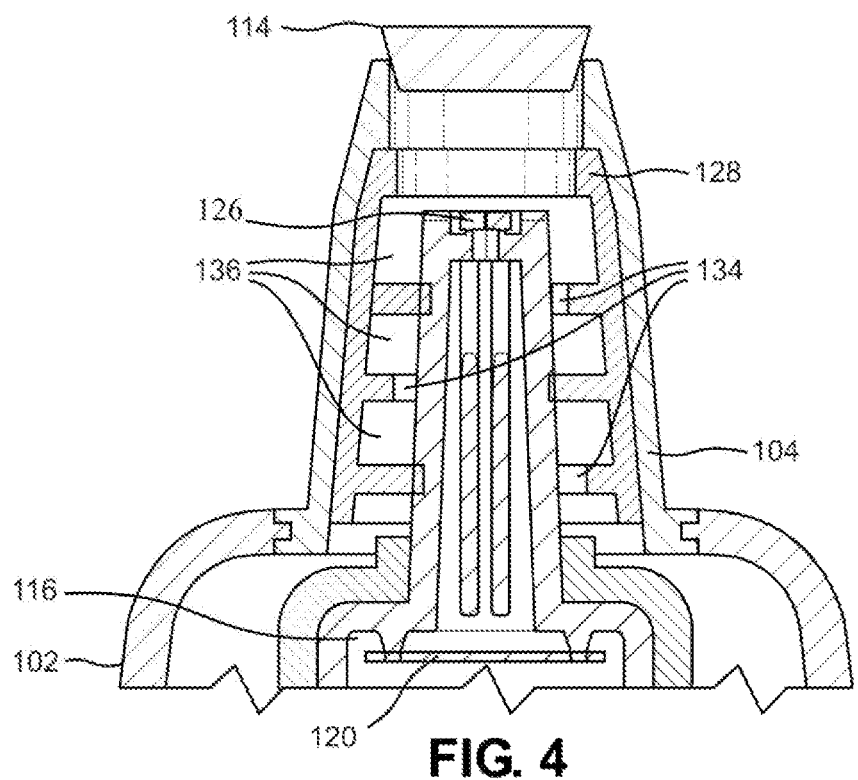
FIG. 4 is a partial cross-sectional view, not to scale, of the sealing material in the fluid outlet nozzle of the device of FIG. 3.

When the fluid outlet nozzle 104 is capped with a plug 114 as shown in FIG. 4, the chambers 136 provide areas for holding humid air so that any fluid on the surface 128 of the ejection head 126 is less likely to dry out between uses of the device 100. Thus chambers 136 provide humidification zones in the fluid outlet nozzle 104 of the device 100 when capped.

Figure 5:
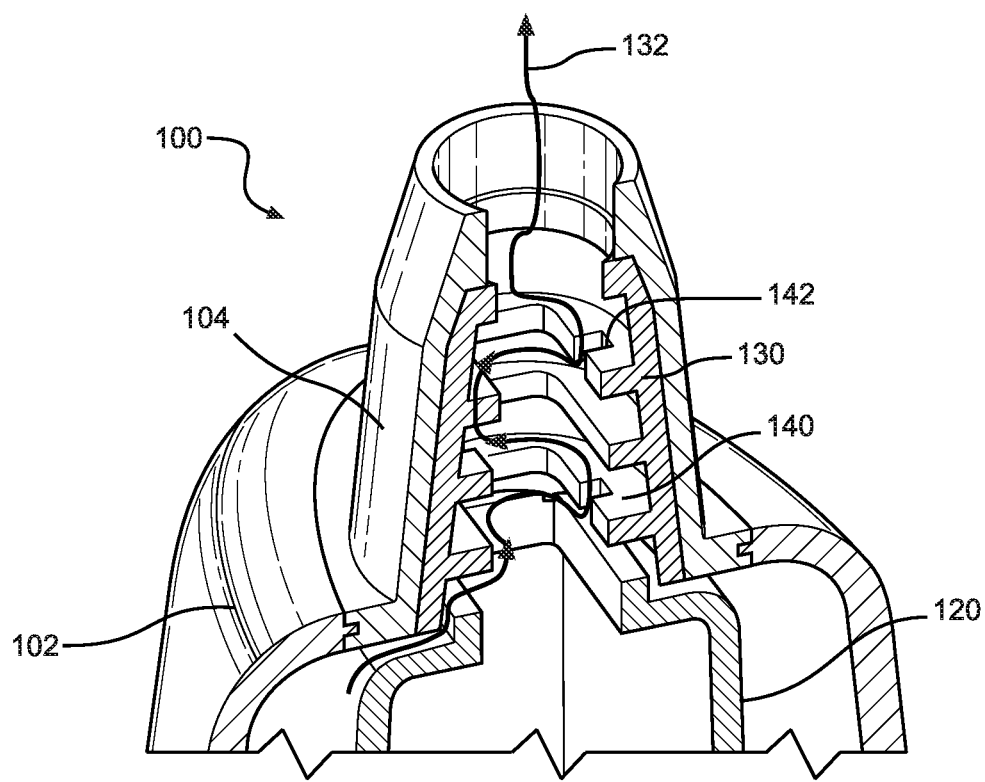
FIG. 5 is a view, not to scale, of the device of FIG. 3 with a fluid jet ejection cartridge removed therefrom.
Figure 6:
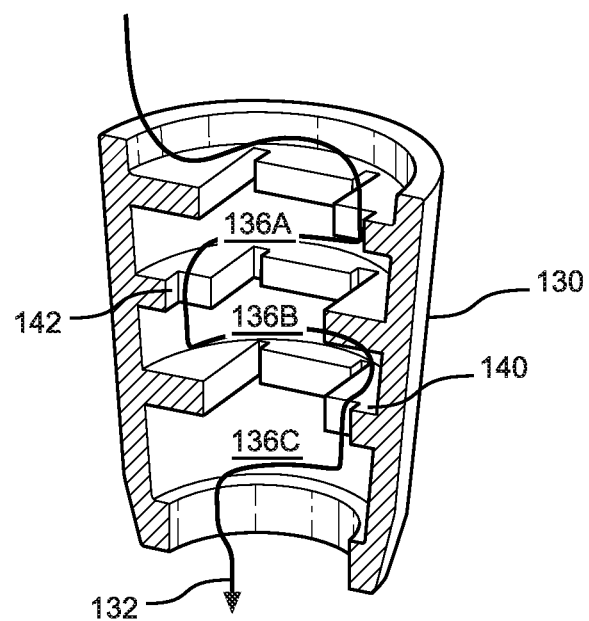
FIG. 6 is a partial view, not to scale, of the sealing material according to the first embodiment of the disclosure.

FIGS. 5 and 6 provide more details of the sealing material 130 and air flow path 132 through the sealing material 130. In the embodiment of FIGS. 3-6, the sealing material 130 contains a plurality of separators 140 that divide the sealing material into the chambers 136A-C illustrated in FIG. 6. Each of the separators 140 has a notch 142 therein, wherein the notches 142 in adjacent separators 140 are on opposite sides of the fluid jet ejection cartridge 116 thereby providing the serpentine air flow path 132 around the fluid jet ejection cartridge 116. In the embodiments illustrated in FIGS. 3-6, the sealing material 130 contains at least three separators 140 providing three chambers 136A-C.

In other embodiments, illustrated in FIGS. 7-8 and 11-12, and the sealing material contains a serpentine air flow path that devoid of the air chambers and notches and is selected to have a much greater length than the cross-sectional air flow area of the flow path. In some embodiments, the serpentine air flow path has a length to area ratio ranging from about 30:1 to about 100:1, such as from about 35:1 to about 60:1.

Figure 7:
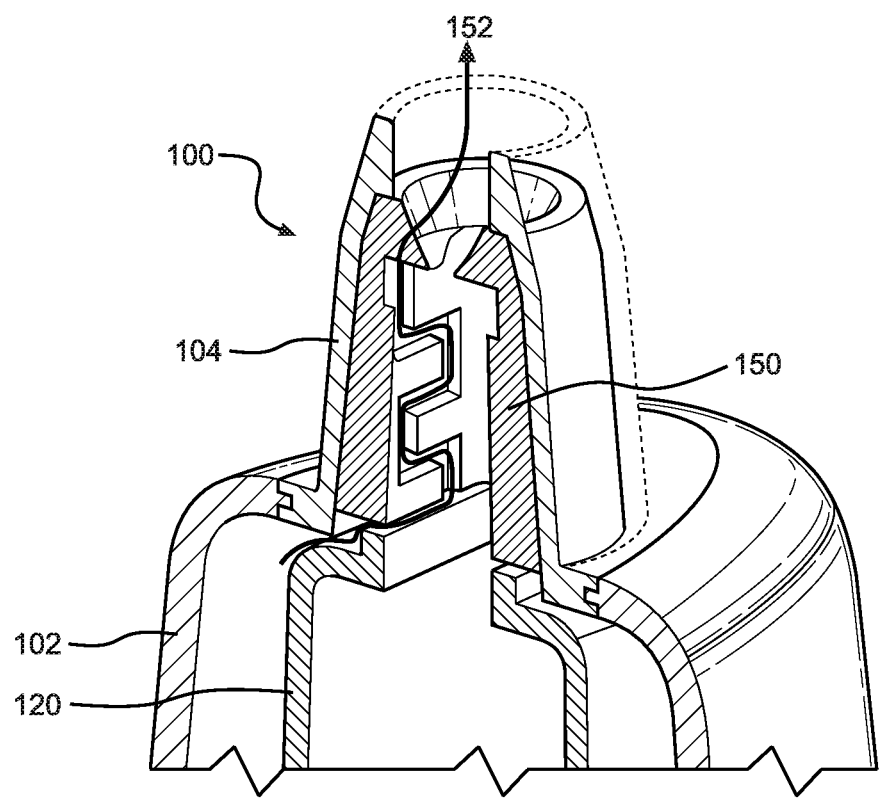
FIG. 7 is a partial perspective, cross-sectional view, not to scale, of the drug delivery device of FIG. 2 containing a sealing material according to a second embodiment of the disclosure.
Figure 8:
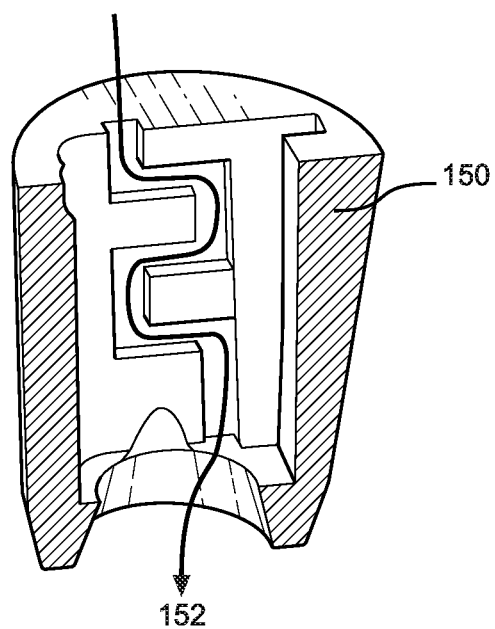
FIG. 8 is a partial view, not to scale, of the sealing material according to the second embodiment of the disclosure.

An alternative configuration of a sealing material 150 for device 100 is illustrated in FIGS. 7 and 8. According to this embodiment, the sealing material 150 contains one or more serpentine air flow paths 152 adjacent to the fluid jet ejection cartridge 116 rather than the separators 140 and chambers 136 described above. At least two serpentine air flow paths 152 are provided in sealing material 150, and the two serpentine air flow paths 152 are on opposite sides of the fluid jet ejection cartridge 116. In order to provide a sufficient humidification zone, when the device 100 is capped, the sealing material 150 may contain three or four serpentine air flow paths 152 around the inside circumference thereof.

Figure 9:
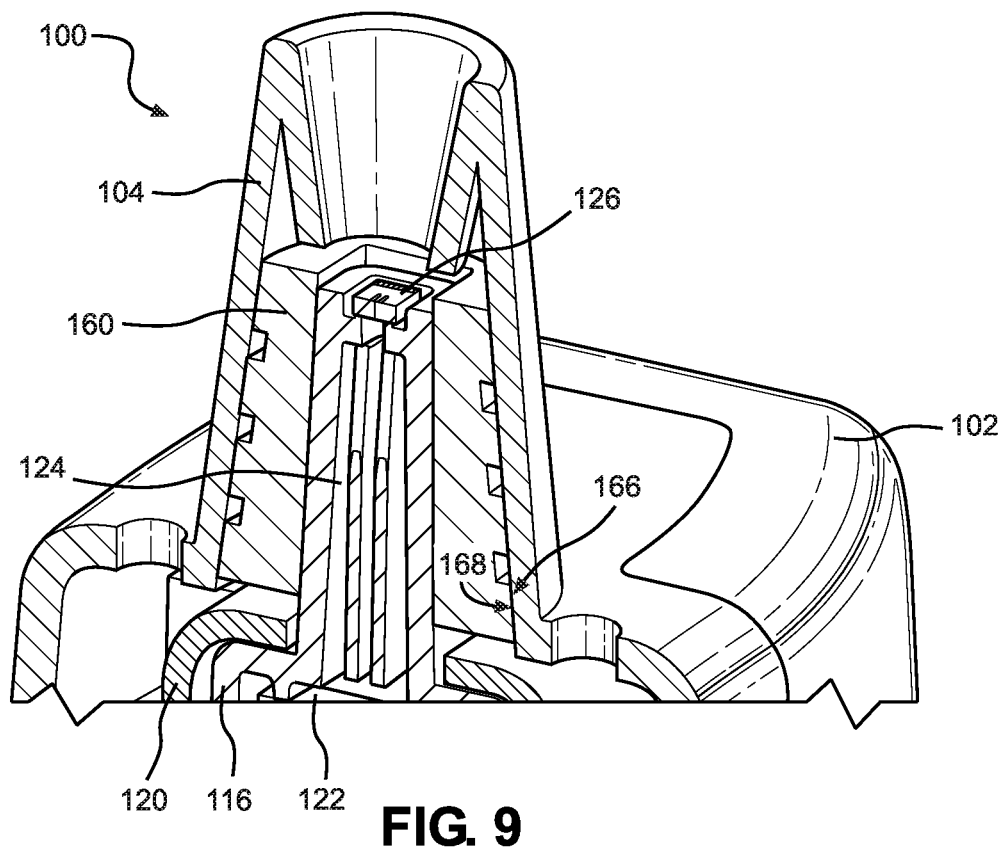
FIG. 9 is a partial perspective, cross-sectional view, not to scale, of the drug delivery device of FIG. 2 containing a sealing material according to a third embodiment of the disclosure.
Figure 10:
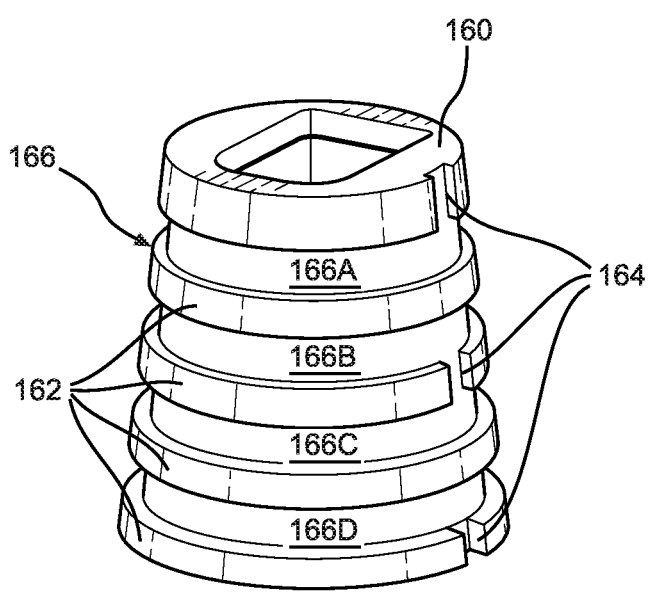
FIG. 10 is a perspective view, not to scale, of the sealing material according to the third embodiment of the disclosure.
Figure 11:
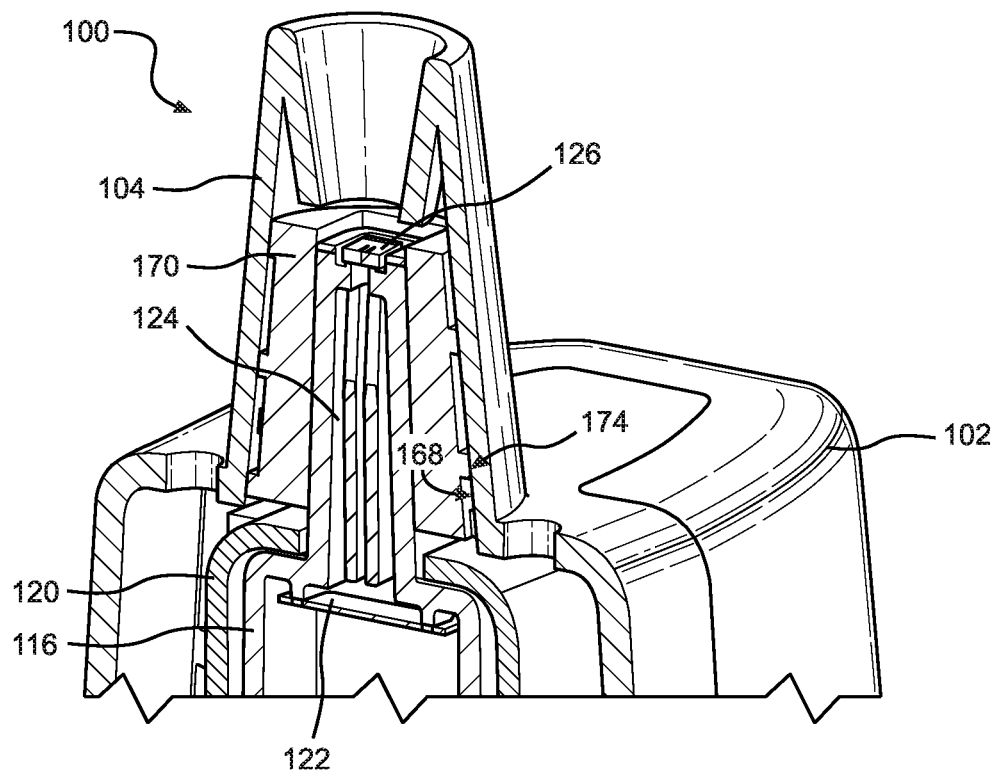
FIG. 11 is a partial perspective, cross-sectional view, not to scale, of the drug delivery device of FIG. 2 containing a sealing material according to a fourth embodiment of the disclosure.
Figure 12:
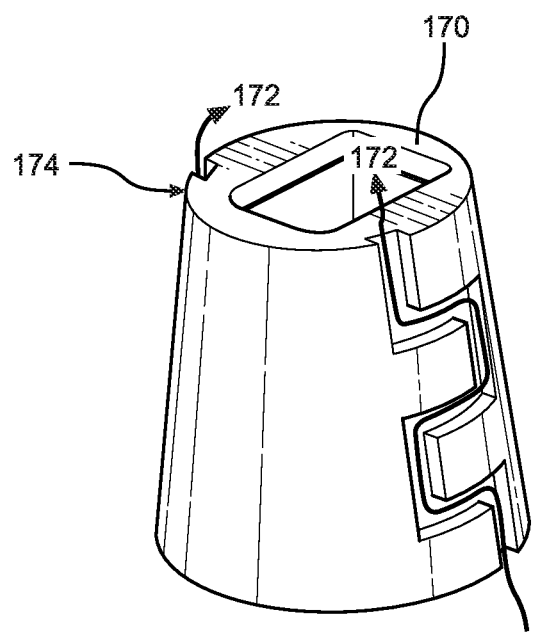
FIG. 12 is a perspective view, not to scale, of the sealing material according to the fourth embodiment of the disclosure.

In other embodiments, the elongate serpentine air flow paths may be positioned on an exterior surface of the sealing material rather than on an inside surface adjacent to the fluid jet ejection cartridge 116. FIGS. 10-12 illustrate alternative embodiments for sealing materials 160 and 170. In FIGS. 9 and 10, the sealing material 160 includes separator rings 162 having alternating notches 164 therein to provide chambers 166A-166D between the separator rings 162. Accordingly, the notches 164 may be on opposite sides of the sealing material 160 in order to provide a serpentine path for air flow in the fluid outlet nozzle 104 between an exterior surface 166 of the sealing material 160 and an interior surface 168 of the fluid outlet nozzle 104.

In FIGS. 11 and 12, the sealing material 170 includes serpentine paths 172 on opposing sides of the sealing material 170. As with the previous embodiment, the serpentine paths 172 are disposed between an inside surface 168 of the fluid outlet nozzle 104 and an outside surface 174 of the sealing material 170. Two serpentine paths 172 are illustrated in FIG. 12, however, the sealing material 170 may contain up to four serpentine paths 172 around a circumference of the sealing material 170. With all of the embodiments described above, when the plug 114 is used to cap the device 100, the serpentine paths and chamber provide a humidification zone between the fluid outlet nozzle 104 and the fluid jet ejection cartridge 116 in order to prevent the ejection head 126 from drying out between uses.

In the embodiments, illustrated in FIGS. 7-8 and 11-12, and the sealing materials 150 and 170 contain serpentine air flow paths 152 and 172, respectively, that are devoid of the air chambers and notches and are selected to have much greater lengths than the cross-sectional air flow areas of the air flow paths. In some embodiments, the serpentine air flow paths have a length to area ratio ranging from about 30:1 to about 100:1, such as from about 35:1 to about 60:1.

It is noted that, as used in this specification and the appended claims, the singular forms "a," "an," and "the," include plural referents unless expressly and unequivocally limited to one referent. As used herein, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A pharmaceutical drug delivery device comprising:
   a drug delivery device body;
   a fluid outlet nozzle attached to the drug delivery device body;
   a fluid jet ejection cartridge containing a liquid pharmaceutical drug is disposed in the drug delivery device body, wherein a fluid ejection head is attached to the fluid jet ejection cartridge and the fluid ejection head is in fluid flow communication with the fluid outlet nozzle; and
   an elongate, serpentine air flow path between an outer surface of the fluid jet ejection cartridge and an inner surface of the fluid outlet nozzle, wherein the elongate, serpentine air flow path provides a reduced pressure differential adjacent to a surface of the fluid ejection head upon use of the drug delivery device and provides a humidification zone.

2. The pharmaceutical drug delivery device of claim 1, wherein the elongate, serpentine air flow path has a length to cross-sectional area ratio of greater than 30:1 to about 100:1.

3. The pharmaceutical drug delivery device of claim 1, wherein the elongate, serpentine air flow path is provided by a multi-chamber sealing material disposed in the fluid outlet nozzle between an interior surface of the fluid outlet nozzle and an exterior surface of the fluid jet ejection cartridge, wherein the multi-chamber sealing material comprises air chambers and notches for air flow between adjacent air chambers.

4. The pharmaceutical drug delivery device of claim 3, wherein the elongate, serpentine air flow path is provided between an exterior surface of the fluid jet ejection cartridge through the notches and air chambers of the multi-chamber sealing material.

5. The pharmaceutical drug delivery device of claim 1, wherein the elongate, serpentine air flow path is provided between an interior surface of the fluid outlet nozzle and an exterior surface of a sealing material disposed in the fluid outlet nozzle adjacent to the fluid jet ejection cartridge.

6. The pharmaceutical drug delivery device of claim 1, further comprising a plug to cap off the fluid outlet nozzle and create the humidification zone in the drug delivery device between uses.

7. A method for reducing a pressure differential on a fluid jet ejection head for a nasal spray device, the method comprising:
   providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge;
   inserting a sealing material between an outer surface of the fluid jet ejection cartridge and an inner surface of the fluid outlet nozzle, wherein the sealing material contains an elongate, serpentine air flow path therein to provide a reduced pressure differential adjacent to a surface of the fluid ejection head upon use of the drug delivery device; and
   activating the nasal spray device while flowing air through the drug delivery device body and elongate, serpentine air flow path when the fluid outlet nozzle is inserted into the nasal passage of a user thereby preventing fluid from drooling from the fluid ejection head.

8. The method of claim 7, wherein the elongate, serpentine air flow path has a length to cross-sectional area ratio of about 30:1 to about 100:1.

9. The method of claim 7, wherein the reduced pressure differential is provided by a multi-chamber sealing material disposed in the fluid outlet nozzle, wherein the multi-chamber sealing material comprises air chambers and notches for air flow between adjacent air chambers.

10. The method of claim 9, wherein the reduced pressure differential is provided between the outer surface of the fluid jet ejection cartridge and the air chambers of the multi-chamber sealing material.

11. The method of claim 7, wherein the reduced pressure differential is provided between the inner surface of the fluid outlet nozzle and an exterior surface of a sealing material.

12. A method for preventing a surface of a fluid jet ejection head for a nasal spray device from drying out between uses, the method comprising:
   providing a pharmaceutical drug delivery device having a fluid outlet nozzle attached to a drug delivery device body; a fluid jet ejection cartridge disposed in the drug delivery device body, the fluid jet ejection cartridge containing the fluid ejection head in fluid flow communication with the fluid outlet nozzle and a pharmaceutical drug in the fluid jet ejection cartridge;
   inserting a sealing material between an outer surface of the fluid jet ejection cartridge and an inner surface of the fluid outlet nozzle, wherein the sealing material contains an elongate, serpentine air flow path therein to provide a humidification zone in the drug delivery device adjacent to a surface of the fluid ejection head between uses of the drug delivery device; and
   plugging the fluid outlet nozzle with a cap to prevent drying out of the surface of the fluid jet ejection head.

13. The method of claim 12, wherein the elongate, serpentine air flow path has a length to cross-sectional area ratio of about 30:1 to about 100:1.

14. The method of claim 12, wherein the humidification zone is provided by a multi-chamber sealing material disposed in the fluid outlet nozzle, wherein the multi-chamber sealing material comprises air chambers and notches for air flow between adjacent air chambers.

15. The method of claim 14, wherein the humidification zone is provided between the outer surface of the fluid jet ejection cartridge and chambers of the multi-chamber sealing material.

16. The method of claim 12, wherein the humidification zone is provided between the inner surface of the fluid outlet nozzle and an exterior surface of a sealing material.

* * * * *